(12) United States Patent
Dean et al.

(10) Patent No.: US 10,209,233 B2
(45) Date of Patent: Feb. 19, 2019

(54) HYDROGEN FLUX SENSOR ASSEMBLY

(71) Applicant: ION SCIENCE LIMITED, Cambridge, Cambridgeshire (GB)

(72) Inventors: William Francis Dean, Cambridge (GB); Andrew Witty, Hertford (GB); Matthew Brady, Great Cambourne (GB); Aki Laakso, Cambridge (GB)

(*) Notice: Subject to any disclaimer, the term of this patent is extended or adjusted under 35 U.S.C. 154(b) by 0 days.

(21) Appl. No.: 15/748,460

(22) PCT Filed: Jul. 27, 2016

(86) PCT No.: PCT/IB2016/054482
§ 371 (c)(1),
(2) Date: Jan. 29, 2018

(87) PCT Pub. No.: WO2017/017621
PCT Pub. Date: Feb. 2, 2017

(65) Prior Publication Data
US 2018/0217115 A1    Aug. 2, 2018

(30) Foreign Application Priority Data

Jul. 30, 2015 (GB) .................................. 1513429.9

(51) Int. Cl.
*G01D 21/00* (2006.01)
*G01N 33/00* (2006.01)
(Continued)

(52) U.S. Cl.
CPC ......... *G01N 33/005* (2013.01); *G01N 15/082* (2013.01); *G01N 33/203* (2013.01)

(58) Field of Classification Search
CPC ... G01N 33/005; G01N 15/082; G01N 33/203
(Continued)

(56) References Cited

U.S. PATENT DOCUMENTS

| 6,637,253 B2* | 10/2003 | Dean ........................ G01N 1/24 |
| | | 73/23.2 |
| 9,857,349 B2* | 1/2018 | Valentini .............. G01N 33/203 |

FOREIGN PATENT DOCUMENTS

| EP | 1114992 B1 | 5/2005 |
| GB | 2312279 B | 10/1997 |
| GB | 2358060 B | 7/2001 |

OTHER PUBLICATIONS

Frank Dean et al.: "Applications of Hydrogen Flux Monitoring to Pre-weld Bakeouts of Steel", NACE International Corrosion Conference 2004, No. 04478, Mar. 28, 2004.

* cited by examiner

Primary Examiner — Helen Kwok
Assistant Examiner — Nashmiya Fayyaz
(74) *Attorney, Agent, or Firm* — Shalom Wertsberger; Saltamar Innovations

(57) ABSTRACT

An analyte sensing probe for attachment to a ferromagnetic surface, the probe comprising a flexible collector plate for placing against the surface, the collector plate having a hole in communication with one end of a capillary and defining when placed against the surface a gap through which air may flow from the periphery of the plate to the capillary, the air entraining any analyte passing through the surface for measurement by an instrument connected in use to the capillary, wherein, in order to cause the collector plate to conform to the surface, the probe further comprises a flexible magnetic assembly positioned on the side of the collector plate remote from the surface, the assembly being composed of a plurality of mutually articulated segments of which at least some are magnetically attracted to the surface.

11 Claims, 3 Drawing Sheets

(51) Int. Cl.
*G01N 15/08* (2006.01)
*G01N 33/20* (2006.01)

(58) Field of Classification Search
USPC .............................. 73/866.5, 863.71, 864.21
See application file for complete search history.

HYDROGEN FLUX SENSOR ASSEMBLY

FIELD OF THE INVENTION

This invention relates to an analyte sensing probe for attachment to a ferromagnetic surface, to sense an analyte, such as hydrogen, issuing from the surface.

BACKGROUND OF THE INVENTION

Hydrogen is able to permeate and seep through almost all metals to a measurable extent. The phenomenon is well known in respect of various steels. In the case of ferritic steels, which include by way of example steel commonly known as carbon steel or mild steel, at temperatures below about 100° C., hydrogen which has permeated into the steel is the cause of a very deleterious failure mechanism known as hydrogen induced cracking (HIC). Usually HIC results from high concentrations of hydrogen entering steel at the internal steel walls of pipes and vessels, assisted by the chemical interaction of specific corrodants known as hydrogen promoters which are contained therein. The most important of these is hydrogen sulphide, a common constituent of crude oil, natural gas, and of refinery processes concerned with the separation of sulphur compounds from oil.

At temperatures exceeding about 100° C. the steel, HIC disappears as a concern. Increase in temperature is attended with a very much increased hydrogen permeability of hydrogen through the steel. Therefore at higher temperatures any type of corrosion which generates hydrogen causes an appreciable amount of hydrogen to permeate steel, such as may be caused by corrosion of steel by organic acids generically known as naphthenic acid, during the distillation of oil containing them, which typically occurs in the temperature range of 200 to 400° C.

In both the above examples of hydrogen permeation it is advantageous to be able to measure the hydrogen flux exiting the external face of a pipe or vessel whose internal face is prospectively corroding. On occasion this may provide an indication of crack risk arising from the corrosion activity, or a measure of the corrosion itself. In either case, the measure of a high hydrogen flux provides a means of assessing the effectiveness of a variety of means of corrosion mitigation to be assessed.

Another application for the flux measurement is upon steel vessels and pipes which are heat treated prior to welding, in order to remove hydrogen in a process known as a hydrogen bakeout. The aim of this process is to avoid hydrogen being trapped in steel in appreciable quantities, which in the absence of such a bakeout may cause subsequent to welding a form of HIC known as stress oriented hydrogen induced cracking (SOHIC). The measurement of flux exiting steel during a hydrogen bakeout may be used to indicate whether a bakeout is needed, if a bakeout is complete, or, most significantly, that further bakeout time is required for the hydrogen exiting the steel to a level associated with a low residual concentration in the steel, whereupon it is safe for welding to proceed without appreciable risk of SOHIC.

In the Applicants' GB Patent 2312279, there is described a hydrogen detection system which is currently in general use in the measurement of hydrogen flux. In this system, air is drawn, by means of a pump, into a probe member that is held against a steel surface. Hydrogen emanating from steel surface under the collector is entrained in the air stream. From there, the air stream is drawn into a central capillary emanating from the probe, and caused to flow across a hydrogen sensor.

In GB 2358060, there is a hydrogen collector comprising a plate which is flexible and has on one major face raised grooves, which upon being appressed to a steel surface, forms the side walls of channels between the steel surface and one collector plate major face. This causes an air stream drawn into the gaseous space between the hydrogen collector major face and the steel surface to efficiently and reliably sweep up hydrogen emanating from the steel surface and into a capillary exiting from the opposing major face of the collector. For most effective collection of hydrogen flux in an air stream conveyed between the deformable plate and tested steel, it is beneficial for the capillary in the collector plate to be placed approximately centrally in an approximately circular plate.

GB 2358060 teaches that the collector plate may be held magnetically against the steel surface. The present Applicants have considered a number of ways of engaging the collector plate by means of magnets. Options for material deployment and arrangements with magnets affixed to springs or spring like materials are limited by the temperature ranges of application, and the consideration that upon deformation to a highly curved steel surface, the forces exerted on springs can oppose the magnetic attraction of the magnets to the steel which hold the collector plate in place. Problems have also been experienced with demagnetisation at high temperature, damage to the hydrogen collector plate caused by magnetic 'snatching' against the steel surface and by magnetic withdrawal from the steel surface.

SUMMARY OF THE INVENTION

In accordance with the present invention, there is provided an analyte sensing probe for attachment to a ferromagnetic surface, the probe comprising a flexible collector plate for placing against the surface, the collector plate having a hole in communication with one end of a capillary and defining when placed against the surface a gap through which air may flow from the periphery of the plate to the capillary, the air entraining any analyte passing through the surface for measurement by an instrument connected in use to the capillary, wherein, in order to cause the collector plate to conform to the surface, the probe further comprises a flexible magnetic assembly positioned on the side of the collector plate remote from the surface, the assembly being composed of a plurality of mutually articulated segments of which at least some are magnetically attracted to the surface.

It is advantageous for the segments of the magnetic assembly to be connected to each other by means of hinges, secured in place by means of a pin. In this way, the segments of the magnetic assembly can bend freely towards any steel surface to which the underlying collector plate is presented. The articulation of the segments need not however rely on hinges and pivot pins and may instead employ any flexible connection.

The magnetic assembly provides flexibility along an axis which can be aligned with an axis of curvature of the ferromagnetic surface, when the latter is cylindrical.

The segments of the magnetic assembly may be provided with stops to limit articulation in at least one direction and define the maximum deformation of the collector plate to which it is attached.

It is desirable for the segments of the magnetic assembly to be identical design, thereby reducing manufacturing cost.

The use of identical segments also makes the design scalable to larger and smaller probe sizes without significant changes to the segment design. An advantageous separation of probe segments, when constructed into a segmental ensemble, conforming to a flat surface, is approximately 20 mm. To enable accommodation of 15 mm diameter magnets an advantageous length is approximately 40 mm. An advantageous depth is 15 mm.

In some embodiments, the segmental design incorporates a bayonet fitting on at least one segment by means of which the magnetic assembly is connectable to a handle.

It is convenient for the collector plate to be connected to the central capillary issuing from it by means of a central segment, to which the capillary, and a plinth receiving an end of the capillary, may be bolted, welded or brazed.

The magnetic assembly may include a 'secondary' plinth member for attachment and detachment of the assembly to the capillary, and the central member may additionally include an adapter enabling attachment of a handle which has been arranged to be axially freely movable relative to the secondary plinth to accommodate collector movement during use. This ensures unhindered bending of the collector.

It is advantageous for each segment to have protruding feet or ridges on their side proximal to the collector plate, that reduce the thermal contact area and act as defined pressure points where the force of magnetic attachment induced between magnets within at least one two segments is realised.

It is further advantageous for each segment to contain one or more magnetic pockets to receive closely fitting permanent magnets, the pocket having space to accommodate a thin layer of a thermally insulating material to intervene between the magnet and the underlying collector plate, so as to insulate the magnets further from any excessive heat issuing from a hot steel surface.

It is further advantageous for the segment pockets to have fixable lids which secure the magnets in place, and for such lids to have vent holes to enable heat to issue from the magnets more freely by means of convective cooling.

It is preferable for the segments to be formed from stainless steel as it is weather-proof, thermally resilient and has a relatively low thermal conductivity as compared with many other metals. Stainless steel is also compatible with a range of manufacturing methods.

BRIEF DESCRIPTION OF THE DRAWINGS

The invention will now be described further, by way of example, with reference to the accompanying drawings, in which.

DETAILED DESCRIPTION OF THE DRAWINGS

FIGS. 1 to 5 show representations of an embodiment of the hydrogen flux probe that is positioned against a cylindrically curved surface 30 to detect hydrogen emanating from the surface 30. The probe comprises a deformable steel collector plate 10 having a central capillary 12 issuing from it centre and supported in place by means of a plinth 14.

Figure 1:
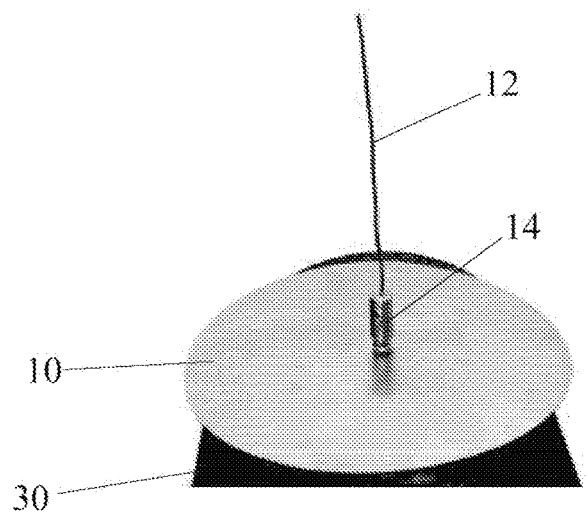
FIG. 1 shows the collector plate and capillary of a probe resting against the outer surface of a tube.
Figure 2:
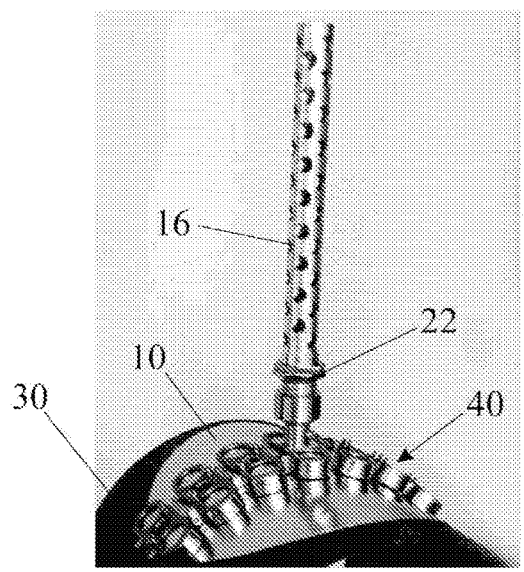
FIG. 2 shows an assembled probe, of which the collector plate is connected to a handle and is bent by a flexible magnetic chain-like assembly to conform closely to the outer surface of the tube.
Figure 3:
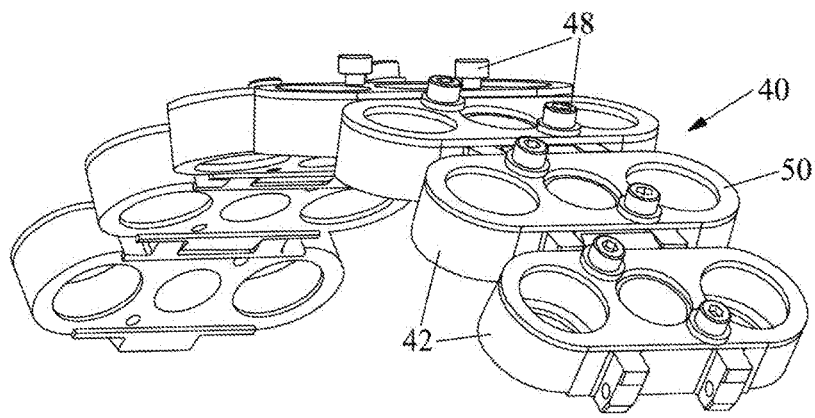
FIG. 3 is a perspective view of the flexible magnetic assembly.
Figure 4:
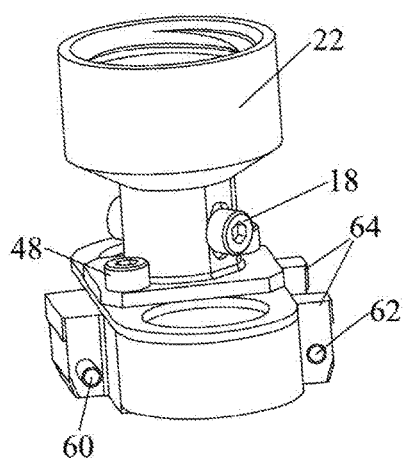
FIG. 4 shows a perspective view of the segment of the magnetic assembly that is connected to the handle and to a plinth that connects the capillary to the collector plate in line with a hole in the collector plate.
Figure 5:
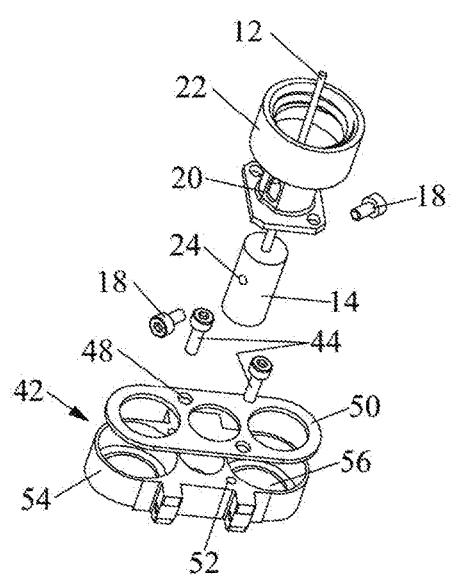
FIG. 5 shows an exploded view of the segment shown in FIG. 4.

As best shown in the exploded view of FIG. 5, the capillary 12, which passes through the centre of a tubular handle 16, is fixed to the plinth 14 by means of two bolts 18 which pass through slots 20 in a handle adaptor 22 and then engage in screw threaded holes 24 in the plinth 14. As an alternative, the capillary 12 may be welded or brazed to the plinth 14.

To bend the collector plate 10, so that it should conform to the cylindrically curved surface 30, the probe is provided with a chain-like magnetic assembly 40 of mutually pivoted similarly constructed segments 42, which may be of stainless steel, and each of which, as explained below, carries two strong permanent magnets.

The handle 16 and the plinth 14 are connected to the central segment 42 of the magnetic assembly 40. The handle adaptor 22 is secured to the central segment 42 by means of two bolts 44 that are inserted through holes 46 in the handle adaptor 22, and through corresponding holes 48 in a lid 50 of the segment 42, and engage in screw threaded holes 52 is the main body 54 of the segment 42.

The partial confinement of the bolts 18 in the slots 20 affords some freedom of movement of the central segment 40, the handle adaptor 22 and the handle 16, relative to the collector plate 10, the plinth 14, and the capillary 12, during the engagement of the probe with the curved steel surface 30.

For sufficiently sensitive detection of flux over a typical steel surface, it is preferable for the diameter of the collector plate 10 to be approximately 150 mm. The central segment 42 of the magnetic assembly 40 is shown as being connected to six other similarly constructed segments 20 which are conveniently sized to straddle this diameter.

The body 54 of each segment 42 comprises two pockets 56 each accommodating a spacer disk of a thermally insulating material and a preferably close fitting permanent magnet, not shown in the drawings in the interest of clarity. Adjoining segments are connected to one another by means of pins 60, slotted through co-aligned holes 62 in hinges 64. The insulation discs and magnets are constrained by the lid 50. Angled abutments at the lower ends of the hinges 64 limit the pivoting movement between adjoining segments 42.

The use of identical segments makes the design scalable to larger and smaller probe sizes without significant changes to the segment design. An advantageous separation of segments, when constructed into a segmental ensemble, conforming to a flat surface, may be approximately 20 mm. To enable accommodation of 15 mm diameter magnets, the segments may have a length of about 40 mm and a depth of about 15 mm.

Figure 6:
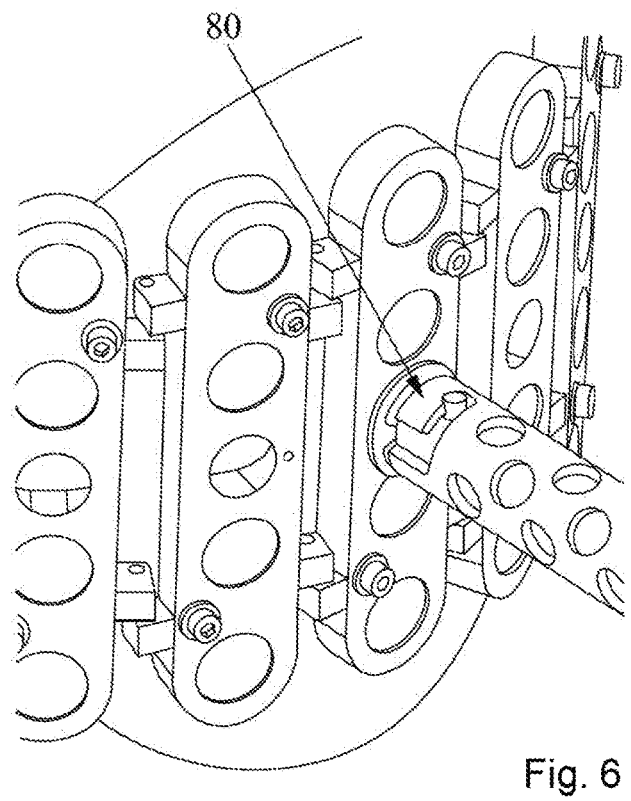
FIG. 6 shows a detail of an embodiment in which a bayonet fitting is used to connect the handle to the plinth.

FIG. 6 shows that instead of screw threading the handle 16 into an adapter 22 bolted to a segment, a bayonet fitting 80 may be used to connect the two to one another, allowing for quicker assembly and release.

Figure 7:
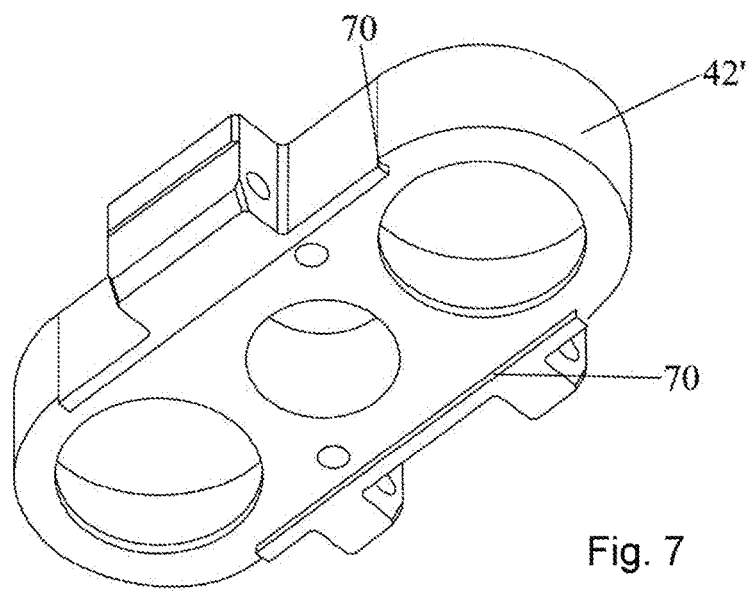
FIG. 7 is a perspective view from below of an alternative segment design that has projecting ridges on its face contacting the collector plate to act as feet.

FIG. 7 shows an alternative design of segment 42' that has protruding ridges 70 along its longer sides that act as feet to limit the area of contact between the magnetic assembly 40 and the collector plate 10. By this means there are two contact points per segment, rather than one, which encourages curvature along the length of the entire segment (right to the outer edge of the end segments). The segment feet also serve to reduce the thermal contact with the collector plate, hence reducing the heat transferred from a hot steel surface, and enabling the ensemble to be engaged on steel surfaces of higher temperature than would be tolerated by magnets contained within at least two segments.

In operation, the probe is placed using the handle 16 against a surface, which may be either flat or cylindrically curved. The magnetic attraction between the magnetic assembly 40 and the surface 30 will bend the collector plate 10 to the extent necessary for it to conform to the surface 30. The opposite end of the capillary 12 is connected to a sensing apparatus that draws air into a gap between the collector plate 10 and the surface 30 and in the process entrains the analyte, such as hydrogen, emanating from the surface 30. The sensing apparatus then analyses the drawn air to measure the analyte concentration.

The invention claimed is:

1. An analyte sensing probe for attachment to a ferromagnetic surface, the probe comprising a flexible collector plate for placing against the surface, the collector plate having at least one side and hole in communication with one end of a capillary and defining when placed against the surface, a gap through which air may flow from the periphery of the plate to the capillary, the air entraining any analyte passing through the surface for measurement by an instrument connected in use to the capillary, wherein the probe further comprises a flexible magnetic assembly positioned on the side of the collector plate remote from the surface, the assembly being composed of a plurality of mutually articulated segments of which at least some are magnetically attracted to the surface; wherein the segments of the magnetic assembly are connected to each other by hinges, secured in place by at least one pin.

2. A probe as claimed in claim 1, wherein the segments of magnetic assembly are provided with stops to limit articulation in at least one direction.

3. A probe as claimed in claim 1, wherein the segments of the magnetic assembly are of identical design.

4. A probe as claimed in claim 1, wherein at least one segment incorporates a fitting by which the magnetic assembly is connectable to a handle.

5. A probe as claimed in claim 1, wherein the collector plate is connected to the capillary by a central reinforcing plinth.

6. A probe as claimed in claim 1, wherein each segment has projecting feet on a segment face proximal to the collector plate.

7. A probe as claimed in claim 1, wherein each segment contains one or more pockets to receive closely fitting permanent magnet or magnets.

8. A probe as claimed in claim 7, wherein each pocket further accommodates a spacer of a thermally insulating material to intervene between the respective magnet or magnets and the collector plate.

9. A probe as claimed in claim 7, wherein the segment pockets have fixable lids which secure the magnets in place.

10. A probe as claimed in claim 9, wherein the pocket lids have vent holes to enable heat to issue from the magnets by convective cooling.

11. A probe as claimed in claim 1, wherein the segments are formed of stainless steel.

\* \* \* \* \*